United States Patent [19]
Loo

[11] 3,988,436
[45] Oct. 26, 1976

[54] SUNSCREENING METHOD USING RICE BRAN OIL

[75] Inventor: Ching C. Loo, Northridge, Calif.

[73] Assignee: Carnation Company, Los Angeles, Calif.

[22] Filed: Feb. 11, 1974

[21] Appl. No.: 441,082

[52] U.S. Cl. ................................ 424/59; 424/47; 424/168
[51] Int. Cl.$^2$ ................................ A61K 7/42
[58] Field of Search ................................ 424/59

[56] References Cited
FOREIGN PATENTS OR APPLICATIONS
2,096,712　2/1972　France ................................ 424/59
　564,609　6/1957　Italy ................................ 424/195

OTHER PUBLICATIONS

Pharmaceutical Formulas, 1944, vol. I, p. 965.
Sagarin Cosmetics Science and Technology, 9/1957, p. 199.

*Primary Examiner*—Dale R. Ore
*Attorney, Agent, or Firm*—Eugene C. Ziehm; Robert D. Kummel

[57] ABSTRACT

Rice bran oil when applied to the skin as such or when incorporated in a pharmaceutically acceptable carrier is effective as a sunscreening agent in protecting the skin against sunburn upon exposure to ultraviolet radiation in the region of from about 2950 to 3150 angstrom units.

3 Claims, No Drawings

SUNSCREENING METHOD USING RICE BRAN OIL

BACKGROUND OF THE INVENTION

This invention relates to a sunscreening agent capable of protecting the skin against sunburn upon exposure to ultraviolet radiation in the 2950 to 3150 angstrom unit range, to compositions containing such a sunscreen agent, and to the method of protecting the human skin against burning upon exposure to sunlight.

It is well known that the burning (erythema) of the skin which follows excessive exposure to sunlight is caused by ultraviolet rays in the wavelength region between 2950 and 3150 angstrom units (A.), while the cosmetically desirable effect of tanning of the skin is due to rays in the wavelength region between about 3150 to 3650 A. Accordingly, a large number of commercial sunscreen compositions are presently marketed in the form of lotions, oils, creams, or the like, which are intended to protect the user against sunburn while permitting tanning to occur. Such commercial compositions contain one or more sunscreening agents which are intended to absorb a substantial portion of the rays in the burning region (2950 to 3150 A.) while allowing transmission of a substantial portion of the rays in the region above 3150 A. Numerous commercially prepared chemical compounds, such as salicylates, para-aminobenzoates, napthoates, and the like have been disclosed in the prior art as having the property of absorbing ultraviolet rays in the 2950–3150 A. region and therefore capable of being used in such commercial compositions.

However, the ability to absorb rays in the burning region is but one of the many properties a material must possess in order to be suitable for use as a sunscreening agent in commercial compositions. The most essential property is a very high absorption of burning rays so that only very small concentrations of the sunscreen agent need be used in the commercial composition. The agent must also have a high ratio of transmittancy of rays in the tanning region to the transmittancy of rays in the burning region so that tanning may occur. In addition, the material must be stable in sunlight, be capable of absorbing burning rays for a period of several hours, be nontoxic, non-irritating and not have any adverse effects on the skin. Moreover, the sunscreen agent should be soluble in a diversity of solvents, including both oils and non-oily substances, so that it can be readily incorporated in the vehicle or base of the commercial composition, but should have a low degree of solubility in water.

Commercially prepared chemical compounds presently being used as sunscreen agents in commercial compositions generally lack one or more of these properties. For example, salicylates have a low absorptive capacity which therefore requires the use of high concentrations of the order of 10% or more in order to be effective. Para-aminobenzoates have the disadvantage of having an analgesic effect on the skin. Naphthoates have poor solubility characteristics and relatively low absorptivities. Moreover, a substantial number of persons do not desire to use compositions containing commercially prepared chemical compounds and would prefer to use sunscreening compositions containing naturally occurring substances. While some naturally occurring substances such as lanolin, peanut oil, sesame oil and petrolatum have been disclosed as being suitable for use as sunscreening agents, such naturally occurring materials which have been suggested heretofore are generally not as effective as chemical sunscreening agents in absorbing high amounts of ultraviolet rays in the burning region.

SUMMARY OF INVENTION

It has been discovered that rice bran oil, when used as such or when incorporated in a pharmaceutically acceptable carrier, is an effective sunscreening agent, absorbing a very high percent of ultraviolet rays in the burning region (2950–3150 A.). It has an extremely high ratio of transmittancy of rays in the tanning region to the transmittancy of rays in the burning region. Rice bran oil is well suited for use as a sunscreening agent for it has excellent stability upon exposure to sunlight, remains effective for a number of hours, does not discolor or develop odor on exposure to sunlight, is both nontoxic and non-irritating to the skin, and is soluble in oils and common solvents so that it can be compounded and formulated into oils, lotions, creams, and the like for ready application to the skin.

DESCRIPTION OF PREFERRED EMBODIMENTS

Rice bran oil is obtained from rice bran by conventional expression and solvent extraction techniques well known in the art, using a variety of solvents such as hexane, ether, and the like. Rice bran oil has a relatively low iodine value, a high oleic acid content, is low in saturated fatty acids, and has a low content of fatty acids more unsaturated than linoleic acid. Typical characteristics of rice bran oil are set out in Table 1.

TABLE 1

| | |
|---|---|
| Iodine No. | 93–109 |
| Saponification Value | 181–195 |
| Fatty Acids: | (percent) |
| Oleic | 39.2–46.0% |
| Linoleic | 26.5–35.1 |
| Myristic | 0.4– 0.6 |
| Palmitic | 11.7–16.4 |
| Stearic | 1.7– 2.7 |
| Linolenic | 1.1 |
| Arachidic | 0.4– 0.6 |
| Gadoleic | 0.4 |
| Behenic | 0.2 |
| Lignoceric | 0.4– 0.7 |
| Caprylic | 0.1 |
| Capric | 0.1 |
| Lauric | 0.1 |

Rice bran oil has been used heretofore in the making of soap, as a salad and cooking oil, and for making hydrogenated shortening.

According to the present invention, it has been found that rice bran oil is an extremely effective sunscreening agent, absorbing a very high percentage of ultraviolet radiation throughout the burning region (2950–3150 A.). The absorption of burning rays by rice bran oil has been found to be many times greater than other naturally occurring substances which have been suggested heretofore as sunscreening agents, as well as commercial sunscreen compositions contaning chemical sunscreen agents. Moreover, rice bran oil has an extremely high differential of greater absorption of burning rays than tanning rays (3150–3650 A.). This absorption differential, which is the ratio of transmittancy of rays in the tanning region to transmittancy of rays in the burning region is many times higher for rice bran oil than for other sunscreening agents or compositions. Such a high absorption differential means that the amount of tanning rays transmitting through the material is high compared to the amount of burning rays transmitted, a characteristic which is extremely desirable in a material intended to be used as a sunscreening agent to prevent burning while permitting tanning to occur.

Rice bran oil, in addition to absorbing a high percent of ultraviolet rays in the burning region and having a very high absorption differential, has a number of other characteristics which make it well suited for use as a sunscreening agent when applied to the skin as such or incorporated in a pharmaceutically acceptable carrier. For example, it is non-toxic and non-irritating to the skin of all subjects tested, has excellent stability upon exposure to sunlight, retains its effectiveness in absorbing burning rays for several hours, and does not discolor, develop odor or otherwise deteriorate upon exposure to sunlight. In addition, for those persons who prefer to use naturally occurring substances rather than commercially prepared chemicals, rice bran oil provides an excellent alternative to the commercial compositions containing such chemicals as the sunscreening agent. Moreover, it can be compounded and formulated with conventional pharmaceutical carriers into oils, lotions, creams and the like for ready application to the skin and is capable of depositing a continuous and durable film on the skin when applied by itself or incorporated in a pharmaceutically acceptable carrier.

The present invention also includes pharmaceutical sunscreen compositions which contain a minor amount of rice bran oil as a sunscreening agent. Such sunscreen compositions comprise a pharmaceutically acceptable carrier as a major component and rice bran oil in an amount effective to absorb a substantial portion of the burning rays. Any suitable pharmaceutical carrier conventionally used as a vehicle for suntanning oils, lotions, creams, and the like can be utilized. For example, rice bran oil may be used with aliphatic alcohols to form hydroalcoholic lotions, or may be incorporated in oily lotions, emulsified lotions, and the like. Conventional well known cream bases may be used. Liquid compositions of the present invention may, if desired, be packaged as an aerosol using conventional halogenated hydrocarbon propellants. In this regard, it is to be understood that the pharmaceutically acceptable carrier employed in accordance with this embodiment of the invention does not constitute an essential feature of the invention it being only necessary that such carrier provide a vehicle by which the rice bran oil can be effectively applied to the skin.

The amount of rice bran oil incorporated in such a composition depends upon a number of factors including the character of the vehicle and the thickness of the film normally formed on the skin by application thereto of the composition. For example, some cosmetic vehicles, particularly those containing oils, reflect some of the light so that smaller amounts of the sunscreen agent would be required. Generally, the pharmaceutical composition is formulated to contain at least about 0.5% by weight of rice bran oil. Since rice bran oil has no deleterious or harmful effects on the skin, greater concentrations, up to 10% by weight or more of the composition may be used. Preferably the composition contains between about 2% – 5% by weight of rice bran oil. If desired, other materials such as insect repellants, perfumes, other sunscreen agents, or the like may also be incorporated in the pharmaceutical composition. For example, if it is desired to provide a composition which affords protection against both burning and tanning rays, a material, such as lanolin, which absorbs a substantial amount of ultraviolet rays in the tanning region, may be incorporated in the composition.

In use, rice bran oil or the cosmetic composition containing rice bran oil is applied to the skin in any manner appropriate to the specific cosmetic form used and locale being treated. Application every 3 to 4 hours will usually be sufficient to provide adequate protection against sunburn.

EXAMPLE I

A series of comparative tests was made to demonstrate the effectiveness of rice bran oil as a suncreening agent as compared to other materials which have been suggested for use as sunscreening materials, including several commercially available sunscreen compositions. In this series of tests, the material being tested was diluted with spectrograde hexane, and the optical density of the diluted material was determined on a Cary 14 spectrophotometer over the range of from 2950 to 3650 angstrom units. All samples were measured in cuvettes 1 cm. in thickness. Spectrograde hexane was placed in the reference beam to cancel out any absorbence it might contribute. The optical density of the material being tested was recorded over this range and converted to zero dilution by multiplying by the dilution factor. The percent ultraviolet rays transmitted in the 2950 to 3150 A. region and 3150 to 3650 A. region were then determined in the following manner:

$$\text{Percent Transmitted} = \frac{1}{\log^{-1}(\text{optical density})} \times 100$$

The average extinction coefficient of each material tested was determined in the following manner:
Extinction coefficient = the reciprocal of the thickness in centimeters of the medium through which the light must travel to reduce the light intensity to one-tenth of its initial value.

The Absorption Differential was determined in the following manner:

$$\frac{\text{Absorption}}{\text{Differential}} = \frac{\text{Transmittancy of Tanning Rays}}{\text{Transmittancy of Burning Rays}}$$

The results of this series of comparative tests is set out in Table 2.

TABLE 2

| Material | % Ultraviolet Rays Transmitted | | Average Extinction Coefficient 2950–3150 A. | Absorption Differential |
|---|---|---|---|---|
| | Burning Rays 2950–3150 A. | Tanning Rays 3150–3650 A. | | |
| Corn Oil | 8.5 | 53.2 | 28.68 | 6.26 |
| Avocado Oil (decolorized) | 33.7 | 67.8 | 12.35 | 2.01 |
| Lanolin | 8.4 | 13.3 | 27.08 | 1.58 |

TABLE 2-continued

| Material | % Ultraviolet Rays Transmitted | | Average Extinction Coefficient 2950–3150 A. | Absorption Differential |
|---|---|---|---|---|
| | Burning Rays 2950–3150 A. | Tanning Rays 3150–3650 A. | | |
| Olive Oil | 68.1 | 83.3 | 4.20 | 1.22 |
| Peanut Oil | 70.2 | 90.5 | 4.00 | 1.29 |
| Sesame Oil | 88.4 | 91.6 | 3.27 | 1.04 |
| Cottonseed Oil | 54.2 | 86.5 | 7.37 | 1.59 |
| Paraffin (undiluted) | 76.5 | 95.5 | 0.12 | 1.25 |
| Commercial Preparation 1 | 14.1 | 25.5 | 21.29 | 1.81 |
| Commercial Preparation 2 | 57.9 | 76.7 | 5.96 | 1.35 |
| Commercial Preparation 3 | 83.2 | 90.3 | 2.01 | 1.08 |
| Thai Rice Bran Oil | 0.06 | 25.9 | 100.00 | 430.00 |
| U.S. Rice Bran Oil XM 104 | 0.00 | 0.00 | 440.00 | |

Since the extinction coefficient is a measure of the ability of the material to absorb ultraviolet rays in the region being tested, the results of this series of tests clearly show that rice bran oil is significantly superior to other oils and to commercial sunscreen preparations tested in its ability to absorb ultraviolet rays in the burning region. These tests also show that the absorption differential of rice bran oil is many times higher than that of other oils or commercial sunscreen compositions tested. Thus for rice bran oil, the amount of tanning rays transmitted through the material is extremely high compared to the amount of burning rays transmitted, a characteristic which is very desirable in a material to be used as a sunscreen agent.

EXAMPLE II

In order to demonstrate the stability of rice bran oil to sunlight, samples of commercially available rice bran oil were spread in thin layers and exposed to sunlight for a 6-hour period. At the end of this period, the samples were examined, and it was found that there was no change in odor or liquidity of the rice bran oil.

During this 6-hour test period, a sample of the rice bran oil was taken at one-hour intervals and the extinction coefficient of the sample determined according to the procedure described in Example I. The results are set out in Table 3.

TABLE 3

| Hours of Exposure | Average Extinction Coefficient 2950 – 3150 A. |
|---|---|
| 0 | 100.7 |
| 1 | 99.3 |
| 2 | 80.4 |
| 3 | 39.1 |
| 4 | 39.3 |
| 5 | 36.3 |
| 6 | 55.3 |

While there was some deterioration at the end of 3 hours' exposure, it should be noted that the extinction coefficient of rice bran oil even after exposure is superior to that of the materials tested in Example I. These test results clearly show that rice bran oil has sufficient stability to sunlight for sunscreen application.

EXAMPLE III

Examples of sunscreen compositions which may be prepared containing rice bran oil as a sunscreening agent are as follows:

| | Parts by Weight |
|---|---|
| Alcoholic Solution | |
| Rice Bran Oil | 2–4 |
| Methyl Phenyl Polysiloxane | 1–2 |
| Propylene Glycol | 5–10 |
| Alcohol | 70–80 |
| Perfume | 0.5 |
| Water, q.s. to a total of 100 | |
| Oil in Water Emulsion | |
| Rice Bran Oil | 3–5 |
| Mineral Oil, medium viscosity | 2–8 |
| Fatty Acid Esters | 5–10 |
| Glycerine | 3–5 |
| Stearic Acid, triple pressed | 1.5–2.5 |
| Triethanolamine | 1–1.5 |
| Perfume | 0.5 |
| Water, q.s. to a total of 100 | |
| Cream | |
| Rice Bran Oil | 5 |
| Mono and Diglycerides of fat-forming acids | 2 |
| Sorbitol Solution | 18 |
| White petrolatum | 19 |
| Water, q.s. to a total of 100 | |

It will be understood that the above formulations are given for illustration only and are not intended to limit, in any way, the type or composition of sunscreening compositions which may be prepared containing rice bran oil. Thus, although the sunscreen compositions set forth in the examples contain between 2–5% by wt. rice bran oil, it will be understood that rice bran oil is effective as a sunscreening agent in such compositions in a range beginning with at least about 0.5% by wt., as disclosed hereinabove.

I claim:

1. A method of protecting the skin against ultraviolet radiation having a wave length of 2950 to 3150 A. consisting essentially of applying to the skin to be protected rice bran oil in an amount sufficient to absorb ultraviolet radiation having said wave length.

2. The method defined in claim 1 in which the rice bran oil is in a pharmaceutically acceptable carrier, the rice bran oil comprising at least about 0.5% by weight of the carrier.

3. The method defined in claim 2 in which the concentration of the rice bran oil in the carrier is between about 2%–5% by weight of the composition.

* * * * *